US00PP18583P2

(12) United States Plant Patent
Blom

(10) Patent No.: US PP18,583 P2
(45) Date of Patent: Mar. 11, 2008

(54) ***ECHINACEA* PLANT NAMED 'PINK SHUTTLES'**

(50) Latin Name: *Echinacea purpurea*
Varietal Denomination: Pink Shuttles

(76) Inventor: Arie Blom, Waterbieslaan 110, 3452 AR Vleuten (NL)

( * ) Notice: Subject to any disclaimer, the term of this patent is extended or adjusted under 35 U.S.C. 154(b) by 0 days.

(21) Appl. No.: 11/527,811

(22) Filed: Sep. 27, 2006

(51) Int. Cl.
*A01H 5/00* (2006.01)

(52) U.S. Cl. ..... Plt./263
(58) Field of Classification Search ..... Plt./258, Plt./263
See application file for complete search history.

(56) References Cited

PUBLICATIONS

UPOV ROM GTITM Computer Database, GTI Jouve Retrieval Software 2007/02 Citation for 'Pink Shuttles'.*

* cited by examiner

*Primary Examiner*—Wendy Haas
(74) *Attorney, Agent, or Firm*—C. A. Whealy

(57) ABSTRACT

A new and distinct cultivar of *Echinacea* plant named 'Pink Shuttles', characterized by its upright and columnar plant habit; moderately vigorous growth habit; and large conical inflorescences with pale pink-colored ray florets and red purple-colored disc florets.

2 Drawing Sheets

Botanical designation: *Echinacea purpurea.*
Cultivar denomination: 'Pink Shuttles'.

CROSS REFERENCE TO RELATED APPLICATIONS

The present application is related to U.S. Plant patent Ser. No. 11/527,814; *Echinacea* Plant Named *Pink Double Delight'.*

BACKGROUND OF THE INVENTION

The present invention relates to a new and distinct cultivar of *Echinacea* plant, botanically known as *Echinacea purpurea,* and hereinafter referred to by the name 'Pink Shuttles'.

The new *Echinacea* is a product of a planned breeding program conducted by the Inventor in The Netherlands. The objective of the breeding program is to create new compact *Echinacea* cultivars with unique inflorescence form and attractive ray floret coloration.

The new *Echinacea* originated from a cross-pollination in Bovenkarspel, The Netherlands in July, 2003, of a proprietary selection of *Echinacea purpurea* identified as code number Ec 201-01, not patented, as the female, or seed, parent with a proprietary selection of *Echinacea purpurea* identified as code number Ec 202-01, not patented, as the male, or pollen, parent. The new *Echinacea* was discovered and selected by the Inventor as a single flowering plant from within the progeny of the stated cross-pollination grown in a controlled environment in IJsselstein, The Netherlands.

Asexual reproduction of the new *Echinacea* by micropropagation in The Netherlands since 2004, has shown that the unique features of this new *Echinacea* are stable and reproduced true to type in successive generations.

SUMMARY OF THE INVENTION

The cultivar Pink Shuttles has not been observed under all possible environmental conditions. The phenotype may vary somewhat with variations in environment such as temperature and light intensity, without, however, any variance in genotype.

The following traits have been repeatedly observed and are determined to be the unique characteristics of 'Pink Shuttles'. These characteristics in combination distinguish 'Pink Shuttles' as a new and distinct cultivar of *Echinacea:*

1. Upright and columnar plant habit.
2. Moderately vigorous growth habit.
3. Large conical inflorescences with pale pink-colored ray florets and red purple-colored disc florets.

Plants of the new *Echinacea* differ from plants of the female parent selection in the following characteristics:

1. Plants of the new *Echinacea* are more compact than plants of the female parent selection.
2. Plants of the new *Echinacea* are more freely branching than plants of the female parent selection.

Plants of the new *Echinacea* differ from plants of the male parent selection in the following characteristics:

1. Plants of the new *Echinacea* are more freely branching than plants of the male parent selection.
2. Plants of the new *Echinacea* and the male parent selection differ in inflorescence form.

Compared to plants of the cultivar Pink Double Delight, plants of the new *Echinacea* are less freely branching, less freely flowering and differ in inflorescence form.

Plants of the new *Echinacea* can be compared to plants of the *Echinacea* cultivar Razzmatazz, disclosed in U.S. Plant Pat. No. 13,894. In side-by-side comparisons conducted in Vleuten, The Netherlands, plants of the new *Echinacea* differed from plants of the cultivar Razzmatazz in the following characteristics:

1. Plants of the new *Echinacea* were more compact than plants of the cultivar Razzmatazz.
2. Plants of the new *Echinacea* were more freely branching than plants of the cultivar Razzmatazz.

BRIEF DESCRIPTION OF THE PHOTOGRAPHS

The accompanying photographs illustrate the overall appearance of the new *Echinacea*. The photographs show the colors as true as it is reasonably possible to obtain in colored reproductions of this type. Colors in the photographs may differ slightly from the color values cited in the detailed botanical description which accurately describe the colors of the new *Echinacea*.

The photograph on the first sheet comprises a side perspective view of a typical flowering plant of 'Pink Shuttles' grown in a container.

The photograph at the top of the second sheet is a close-up view of a typical inflorescence of 'Pink Shuttles'.

The photograph at the bottom of the second sheet is a close-up view of a typical leaf of 'Pink Shuttles'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in Vleuten, The Netherlands during the summer in an outdoor nursery and under conditions and practices which approximate those generally used in commercial *Echinacea* production. During the production of the plants, day temperatures ranged from −5° C. to 35° C. and night temperatures ranged from −8° C. to 20° C. Measurements and numerical values represent averages for typical flowering plants. Plants were about 16 months year old when the photographs and description were taken.

Botanical classification: *Echinacea purpurea* cultivar Pink Shuttles.

Parentage:

*Female parent.*—Proprietary selection of *Echinacea purpurea* identified as code number Ec 201-01, not patented.

*Male parent.*—Proprietary selection of *Echinacea purpurea* identified as code number Ec 202-01, not patented.

Propagation:

*Type.*—By micropropagation.

*Time to initiate roots.*—About one week at 25° C.

*Time to produce a rooted young plant.*—About five weeks at 21° C.

*Root description.*—Fine, fibrous; pale cream white in color.

*Rooting habit.*—Freely branching; moderately dense.

Plant description:

*Plant form/growth habit.*—Upright and columnar plant habit; basal branching with about three primary branches developing per plant. Moderately vigorous growth habit.

*Plant height.*—About 71.5 cm.

*Plant diameter or spread.*—About 37 cm.

*Basal branches.*—Length: About 52 cm. Diameter: About 4 mm. Internode length: About 6.7 cm. Aspect: Mostly upright. Strength: Strong. Texture: Pubescent; rough. Color: 144A.

Foliage description:

*Arrangement.*—Alternate, simple.

*Length.*—About 12.3 cm.

*Width.*—About 5.2 cm.

*Shape.*—Ovate.

*Apex.*—Acute.

*Base.*—Attenuate.

*Margin.*—Irregularly and sparsely serrate.

*Texture, upper and lower surfaces.*—Pubescent; rough.

*Venation pattern.*—Pinnate.

*Color.*—Developing foliage, upper surface: 137A. Developing foliage, lower surface: 137B to 137C. Fully expanded foliage, upper surface: 137A; venation, 144B. Fully expanded foliage, lower surface: 138A; venation, 144B to 144C.

*Petiole length.*—About 4.7 cm.

*Petiole diameter.*—About 2 mm.

*Petiole texture, upper and lower surfaces.*—Pubescent; rough.

*Petiole color, upper surface.*—144A to 144B.

*Petiole color, lower surface.*—144B to 144C.

Inflorescence description:

*Appearance.*—Rotate single inflorescence form with ray and disc florets. Inflorescences positioned above the foliage on strong peduncles and face upright. About two inflorescences develop per lateral branch. Inflorescences not persistent.

*Fragrance.*—Faint, sweet.

*Time to flower.*—Plants flower continuously from late July to late September in The Netherlands.

*Inflorescence longevity.*—Inflorescences maintain good substance for about three weeks on the plant.

*Inflorescence bud.*—Height: About 2.2 cm. Diameter: About 2.9 cm. Shape: Broadly ovate. Color: Between 144A and N144A.

*Inflorescence size.*—Diameter: About 7.2 cm. Depth (height): About 5.6 cm. Disc diameter: About 2.4 cm. Receptacle height: About 1.9 cm. Receptacle diameter: About 1.4 cm.

*Ray florets.*—Length: About 3.9 cm. Width: About 1.3 cm. Shape: Oblanceolate. Apex: Praemorse. Base: Cuneate. Margin: Entire. Texture, upper and lower surfaces: Smooth, glabrous. Number of ray florets per inflorescence: About 13 arranged in a single whorl. Aspect: Drooping. Color: When opening and fully opened, upper surface: 70C; towards the apex, 70D; apex, 144B. With development, 156A to 156B; apex, 144C to 144D; towards the base, 182D. When opening, lower surface: 182D; apex, 144B. With development, 144B to 144C tinted with 182D.

*Disc florets.*—Length: About 1.4 cm. Diameter: About 4 mm. Shape: Tubular, enlarged; apices acute. Number of disc florets per inflorescence: About 400. Texture, upper and lower surfaces: Smooth, glabrous. Color: Immature, inner and outer surfaces: 54A. Mature, inner surface: 63A. Mature, outer surface: 63B.

*Receptacle spines.*—Quantity: One per disc floret. Shape: Acicular. Apex: Acute. Base: Attenuate. Texture: Smooth, glabrous. Color: Apex: 25A to 25B; at apex, N34A. Mid-section: 143A. Base: 145C to 145D.

*Involucral bracts.*—Quantity per inflorescence: About 54 in about three whorls. Length: About 8 mm. Width: About 1.5 mm. Shape: Lanceolate. Apex: Acute. Base: Cuneate. Margin: Entire. Texture, upper surface: Smooth, glabrous. Texture, lower surface: Densely pubescent. Color, upper surface: 143A to 143B. Color, lower surface: 143B to 143C.

*Peduncles.*—Length: About 15.8 cm. Diameter: About 3 mm. Strength: Strong. Aspect: Mostly upright. Texture: Pubescent; rough. Color: 144B.

*Reproductive organs.*—Androecium: Quantity per disc floret: Three. Filament length: About 2 mm. Filament color: 165C to 165D. Anther shape: None observed. Gynoecium: Pistil length: About 6 mm. Stigma shape: Cleft; reflexed. Stigma color: 59A. Style length: About 4 mm. Style color: 60B to 60D. Ovary color: 157D. Fruits/seeds: Fruit and seed development have not been observed.

Disease/pest resistance: Plants of the new *Echinacea* have not been shown to be resistant to pathogens and pests common to *Echinacea.*

Garden performance: Plants of the new *Echinacea* have exhibited good tolerance to rain and wind, have been observed to be hardy to USDA Zone 4 and to tolerate high temperatures of about 35° C.

It is claimed:

1. A new and distinct *Echinacea* plant named 'Pink Shuttles' as illustrated and described.

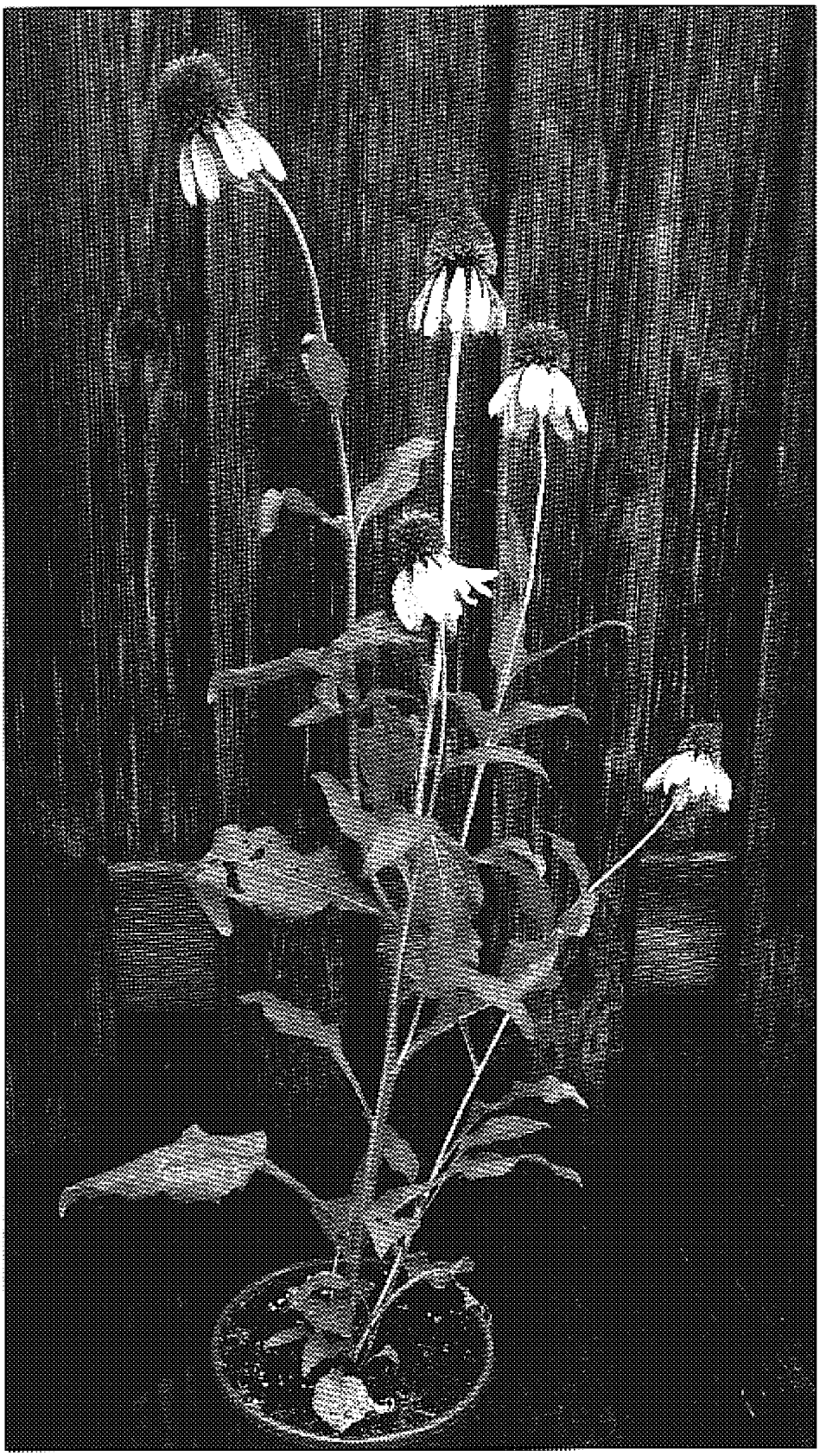

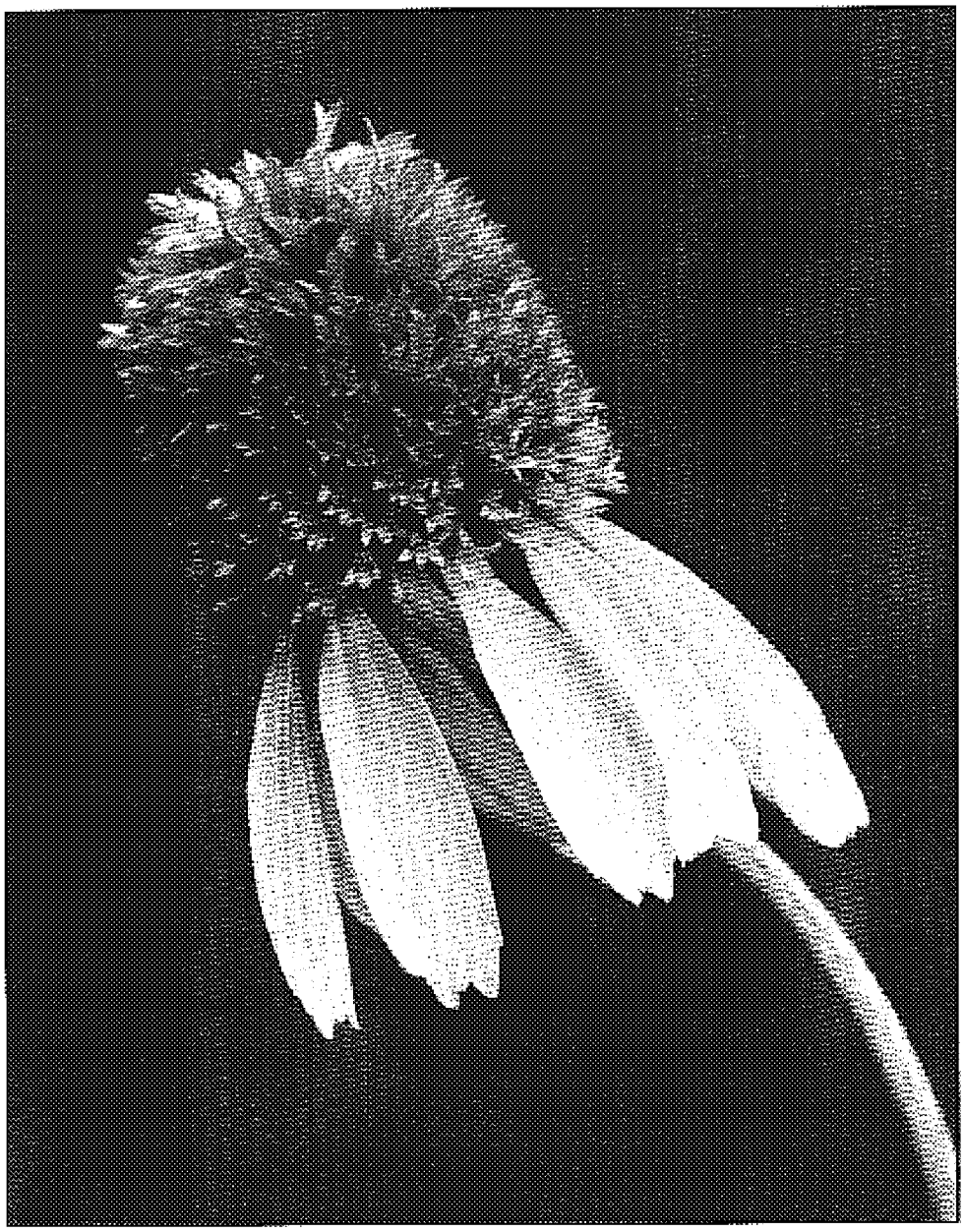
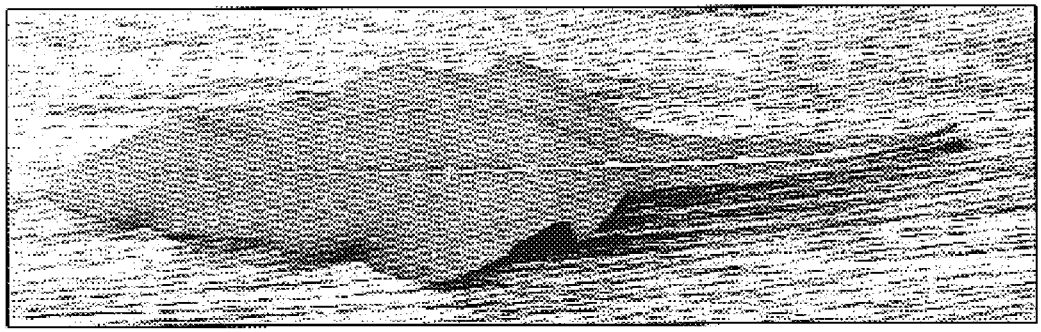

* * * * *